United States Patent
Swedberg et al.

(10) Patent No.: US 10,973,711 B2
(45) Date of Patent: Apr. 13, 2021

(54) ABSORBENT ARTICLE AND METHOD OF MANUFACTURING SAME

(71) Applicant: Essity Hygiene and Health Aktiebolag, Gothenburg (SE)

(72) Inventors: Maria Swedberg, Kungsbacka (SE); Anders Silfverstrand, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/956,238

(22) PCT Filed: Dec. 22, 2017

(86) PCT No.: PCT/EP2017/084476
§ 371 (c)(1),
(2) Date: Jun. 19, 2020

(87) PCT Pub. No.: WO2019/120574
PCT Pub. Date: Jun. 27, 2019

(65) Prior Publication Data
US 2021/0007912 A1    Jan. 14, 2021

(51) Int. Cl.
*A61F 13/62* (2006.01)
*A61F 13/15* (2006.01)
(Continued)

(52) U.S. Cl.
CPC ...... *A61F 13/625* (2013.01); *A61F 13/15756* (2013.01); *B29C 65/08* (2013.01);
(Continued)

(58) Field of Classification Search
None
See application file for complete search history.

(56) References Cited

U.S. PATENT DOCUMENTS

| 5,413,568 A | 5/1995 | Roach et al. |
| 5,531,732 A | 7/1996 | Wood |

(Continued)

FOREIGN PATENT DOCUMENTS

| CN | 1296401 A | 5/2001 |
| CN | 101346118 A | 1/2009 |

(Continued)

OTHER PUBLICATIONS

Chinese Office Action for Chinese Application No. 201680087410.1, dated May 15, 2020, with translation, 26 pages.
(Continued)

*Primary Examiner* — Barbara J Musser
(74) *Attorney, Agent, or Firm* — Buchanan Ingersoll & Rooney P.C.

(57) ABSTRACT

Absorbent article comprising a layered structure with an absorbent material sandwiched between at least two layers of said layered structure, such as for example a diaper, and at least one elongate tab. Each elongate tab comprises an attached portion by which the tab is permanently attached to at least one layer of the layered structure and a fastening portion with hooks provided for releasably engaging a landing zone on the absorbent article. At least the attached portion and the fastening portion of each tab are made of a predetermined material which is deformable by means of an energy source. The attached portion comprises a weld, and the weld of the attached portion and the hooks of the fastening portion are integrally formed deformations of said predetermined material. Method for manufacturing such article, wherein the weld and the hooks are formed simultaneously.

18 Claims, 6 Drawing Sheets

(51) Int. Cl.
    *B29C 65/00*       (2006.01)
    *B29C 65/08*       (2006.01)
    *B29K 701/12*     (2006.01)
    *B29L 31/48*       (2006.01)

(52) U.S. Cl.
    CPC ...... *B29C 66/1122* (2013.01); *B29K 2701/12* (2013.01); *B29L 2031/4878* (2013.01)

(56) References Cited

U.S. PATENT DOCUMENTS

| | | | |
|---|---|---|---|
| 5,785,699 | A | 7/1998 | Schmitz |
| 6,007,527 | A | 12/1999 | Kawaguchi et al. |
| 6,036,679 | A | 3/2000 | Balzar et al. |
| 6,287,665 | B1 | 9/2001 | Hammer |
| 6,746,434 | B2 | 6/2004 | Johnson et al. |
| 7,857,801 | B2 | 12/2010 | Hamall et al. |
| 8,197,458 | B2 | 6/2012 | Baeck |
| 8,298,205 | B2 | 10/2012 | Norrby et al. |
| 8,585,672 | B2 | 11/2013 | Lavon et al. |
| 8,663,184 | B2 | 3/2014 | Liu et al. |
| 8,784,722 | B2 | 7/2014 | Rocha |
| 9,834,355 | B2 | 12/2017 | Dahlqvist et al. |
| 10,076,162 | B2 | 9/2018 | Rocha |
| 2002/0023321 | A1* | 2/2002 | Clune ................ A44B 18/0073 24/306 |
| 2003/0120253 | A1 | 6/2003 | Wentzel et al. |
| 2008/0038507 | A1 | 2/2008 | Seth et al. |
| 2010/0108251 | A1 | 5/2010 | Malowaniec |
| 2010/0180407 | A1 | 7/2010 | Rocha |
| 2017/0087034 | A1 | 3/2017 | Bosser |
| 2019/0016058 | A1* | 1/2019 | Tuma ................ B29C 66/73921 |
| 2019/0224054 | A1 | 7/2019 | Silfverstrand et al. |

FOREIGN PATENT DOCUMENTS

| | | | |
|---|---|---|---|
| CN | 101500521 A | 8/2009 | |
| CN | 101534778 A | 9/2009 | |
| CN | 101641066 A | 2/2010 | |
| CN | 102341228 A | 2/2012 | |
| CN | 106170276 A | 11/2016 | |
| DE | 10102501 A1 | 8/2002 | |
| DE | 10 2016 000 756 A1 | 7/2017 | |
| DE | 102016000756 A1 | 7/2017 | |
| EP | 1529506 A1 | 5/2005 | |
| EP | 2926787 A1 | 10/2015 | |
| JP | H10511868 A | 11/1998 | |
| JP | 2000000269 A | 1/2000 | |
| JP | 2003-535649 A | 12/2003 | |
| JP | 2014104147 A | 6/2014 | |
| RU | 2395265 C1 | 7/2010 | |
| RU | 2396932 C1 | 8/2010 | |
| RU | 2400199 C2 | 9/2010 | |
| RU | 2404057 C2 | 11/2010 | |
| RU | 2 518 212 C2 | 6/2014 | |
| TW | 201545729 A | 12/2015 | |
| WO | 9530397 A1 | 11/1995 | |
| WO | 96/20675 A1 | 7/1996 | |
| WO | 9953881 A1 | 10/1999 | |
| WO | 00/27236 A1 | 5/2000 | |
| WO | WO-0027236 A1 * | 5/2000 | ......... A44B 18/0073 |
| WO | 0197738 A2 | 12/2001 | |
| WO | 0226182 A2 | 4/2002 | |
| WO | 2008060204 A1 | 5/2008 | |
| WO | 2009136826 A1 | 11/2009 | |
| WO | 2010085492 A1 | 7/2010 | |
| WO | 2013162430 A1 | 10/2013 | |
| WO | 2015190964 A1 | 12/2015 | |
| WO | 2015190966 A1 | 12/2015 | |
| WO | 2016081438 A1 | 5/2016 | |
| WO | 2016149243 A1 | 9/2016 | |

OTHER PUBLICATIONS

European Office Action for European Application No. 16734682.4, dated Jun. 19, 2019, 3 pages.
International Preliminary Report on Patentability for Application No. PCT/EP2016/065862, dated Jul. 11, 2018, 6 pages.
Brazil Office Action for Brazil Application No. BR112018076381-0, dated May 18, 2020, 4 pages.
Chinese Office Action for Chinese Application No. 201680087410.1, dated Jan. 19, 2020, with translation, 17 pages.
Chinese Office Action for Chinese Application No. 201680087410.1, dated Jul. 15, 2019, with translation—22 pages.
Chinese Office Action for Chinese Application No. 201680087419.2, dated Jun. 28, 2019, with translation, 16 pages.
International Preliminary Report on Patentability (PCT/IPEA/409) dated Jul. 18, 2018, by the European Patent Office as the International Preliminary Examining Authority for International Application No. PCT/EP2016/065851.
International Preliminary Report on Patentability (PCT/IPEA/409) dated Feb. 27, 2020, by the European Patent Office as the International Preliminary Examining Authority for International Application No. PCT/EP2017/084476.
International Preliminary Report on Patentability (PCT/IPEA/409) dated Mar. 30, 2020, by the European Patent Office as the International Preliminary Examining Authority for International Application No. PCT/EP2017/084479.
International Search Report (PCT/ISA/210) and Written Opinion (PCT/ISA/237) dated Feb. 15, 2017, by the European Patent Office as the International Searching Authority for International Application No. PCT/EP2016/065851.
International Search Report (PCT/ISA/210) and Written Opinion (PCT/ISA/237) dated Jul. 11, 2018, by the European Patent Office as the International Searching Authority for International Application No. PCT/EP2016/065862.
International Search Report (PCT/ISA/210) and Written Opinion (PCT/ISA/237) dated Jun. 27, 2018, by the European Patent Office as the International Searching Authority for International Application No. PCT/EP2017/084479.
International Search Report (PCT/ISA/210) dated Feb. 21, 2018, by the European Patent Office as the International Searching Authority for International Application No. PCT/EP2017/084476.
Notice of Reasons for Rejection for Japanese Application No. 2019-500234, dated Dec. 16, 2019, with translation, 5 pages.
Russian Decision to Grant a Patent for Russian Application No. 2019101795, dated May 24, 2019, with translation, 13 pages.
Written Opinion (PCT/IPEA/408) dated Nov. 15, 2019, by the European Patent Office as the International Preliminary Examining Authority for International Application No. PCT/EP2017/084479.
Non-Final Office Action issued by the U.S. Patent and Trademark Office in U.S. Appl. No. 16/314,234 dated Oct. 8, 2020, U.S. Patent and Trademark Office, Alexandria, VA. (10 pages).
Office Action (Decision to Grant a Patent) dated Jul. 22, 2020, by the Japanese Patent Office in corresponding Japanese Patent Application No. 2019-500234, and an English Translation of the Office Action. (5 pages).
Notification of the First Office Action dated Dec. 16, 2020, by the National Intellectual Property Administration (CNIPA) of the People's Republic of China in corresponding Chinese Patent Application No. 201780097814.3 and an English translation of the Office Action. (23 pages).
Decision to Grant dated Oct. 26, 2020, by the Federal Service for Intellectual Property in Russian Patent Application No. 2020124162 and an English translation of the Decision. (21 pages).
Office Action dated Nov. 30, 2020, by the U.S. Patent and Trademark Office in U.S. Appl. No. 16/955,895. (14 pages).
Decision to Grant a Patent for Invention dated Nov. 24, 2020, by the Federal Service for Intellectual Property (Rospatent) in corresponding Russian Patent Application No. 2020124121 and an English translation of the Decision. (21 pages).

* cited by examiner

ABSORBENT ARTICLE AND METHOD OF MANUFACTURING SAME

FIELD OF THE DISCLOSURE

The present disclosure relates to an absorbent article and a method of manufacturing said absorbent article.

BACKGROUND ART

Known absorbent articles, such as diapers, comprise a layered structure enclosing an absorbent material and at least one elongate tab, such as for example lateral fastening tabs for laterally fastening side panels of the article to each other or a disposal tab which is wrapped around the article when it is thrown away. Such tabs are commonly attached to the layered structure by means of an adhesive and have a fastening portion with hooks provided for releasably engaging a landing zone on another part of the absorbent article.

From U.S. Pat. No. 6,746,434 B2 an absorbent article is known which comprises a garment material of which part of its surface is mechanically modified to form a plurality of surface protrusions integrally from the garment material. The absorbent article further comprises a landing zone having a plurality of fibrous loops adapted to engage with the surface protrusions to provide a fastening mechanism. U.S. Pat. No. 6,746,434 B2 further describes a method for mechanically forming the surface protrusions on the garment material.

A method for forming such surface protrusions on a substrate is further known from WO 2010/085492 A1.

SUMMARY

It is a first aim of the present disclosure to provide an absorbent article of the type comprising a layered structure with an absorbent material sandwiched between at least two layers and at least one elongate tab permanently attached to at least one layer of the layered structure, which is simpler and more economical to manufacture, preferably without the use of adhesive.

It is a second aim of the present disclosure to provide a simpler and more economical method of manufacturing such an absorbent article, preferably without the use of adhesive.

The disclosure provides, according to a first aspect, an absorbent article comprising a layered structure with an absorbent material sandwiched between at least two layers of said layered structure, such as for example a diaper, and at least one elongate tab. Each elongate tab comprises an attached portion by which the tab is permanently attached to at least one layer of the layered structure and a fastening portion with hooks provided for releasably engaging a landing zone on the absorbent article. At least the attached portion and the fastening portion of each tab are made of a predetermined material which is deformable by means of an energy source. The attached portion comprises a weld, and the weld of the attached portion and the hooks of the fastening portion are integrally formed deformations of said predetermined material.

According to the present disclosure, the weld and the hooks of the fastening portion are made of a predetermined material, preferably the same material, at least materials that are deformable by means of an energy source, such as for example heat, ultrasonic vibrations, micro waves, infrared radiation or other. In this way, it is possible to form hooks on the tab and weld the tab onto the layered structure simultaneously, i.e., in the same or substantially the same step in a production line.

In this way, it is also possible to avoid adhesive for attaching the tab to the layered structure. The use of adhesive can be undesirable because it may be hard to control the amount of adhesive that comes out of an adhesive applicator and the adhesive may contaminate the production line. Furthermore, the attachment by means of a weld by deformation of said material can create a stronger permanent attachment.

In embodiments according to the disclosure, the absorbent material sandwiched between at least two layers of said layered structure may be an absorbent core. The layered structure may comprise a liquid-permeable topsheet and a liquid-impermeable backsheet. The absorbent core may be arranged along a longitudinal axis of the layered structure and a transversal axis extending in a perpendicular direction in relation to the longitudinal axis, and said article may define a front portion, a back portion and a crotch portion.

In embodiments according to the disclosure, the at least one elongate tab may comprise a complete layer of said material or may be fully made of said material. Said material is preferably a thermoplastic material. The at least one elongate tab is preferably a film, a (nonwoven) web, a sheet, or a laminate, for example a film and a nonwoven laminated together.

In embodiments according to the disclosure, further hooks may be formed on the weld, said further hooks being integrally formed deformations of the predetermined material of the attached portion and/or of a material of said at least one layer of the layered structure. These further hooks may economically be formed in the same process step as the forming of the hooks of the fastening portion. These further hooks may for example be useful to hold a folded over part of the elongate tab in position during the manufacturing process, i.e., to ensure that the tab stays in folded position.

In embodiments according to the disclosure, the at least one elongate tab may be fastening tabs attached to first side portions of the layered structure and provided for being fastened to landing zones one or more landing zones on a surface of the layered structure, for example to fasten the absorbent article around a wearer's waist.

In embodiments according to the disclosure, the first side portions may be first side panels of the layered structure, for example at a rear body portion of the article, and said landing zones may be provided by second side panels of the layered structure, for example at a front body portion of the article. The first side panels may be made of, or comprise a layer of a nonwoven material, which may also be a thermoplastic material deformable by means of an energy source chosen from: heat, ultrasonic vibrations, micro waves, infrared radiation, preferably deformable by means of the same energy source as the fastening and attached portions of the tab. The weld, and possibly the further hooks on the weld, may thus be formed by deformation of both the material of the attached portion and the material of the first side panels.

In embodiments according to the disclosure, the second side panels of the layered structure may be made of, or comprise a layer of nonwoven material, for example the same nonwoven material as the first side panels, so as to provide the landing zones for the fastening portions of the fastening tabs.

In embodiments according to the disclosure, the fastening tabs may be each welded to a first surface of the respective first side portion and folded such that the fastening portion releasably engages said first surface of the respective first side portion, or a second surface of the respective first side portion opposite the first surface. The further hooks may be provided in the region of the weld so as to releasably engage a further portion of the folded fastening tab In embodiments according to the disclosure, the at least one elongate tab may be a disposal tab attached to an outer layer of the layered structure and provided for being wrapped around the absorbent article. After use, absorbent articles are usually folded or rolled up so that the soiled portion is wrapped inside for disposal. In order to reduce the risk of the soiled article unfolding and to keep the soiled portion inside, it is desired that a so-called disposal tab is arranged to keep the article in the folded or rolled-up state under disposal.

In embodiments according to the disclosure, the disposal tab may be a Z-folded tab, a bottom layer of the Z-folded tab comprising the attached portion which is attached to the outer layer of the layered structure and a top layer of the Z-folded tab comprising the fastening portion with integrally formed hooks, for releasably engaging a first zone on the outer layer of the layered structure while the tab is folded and a second zone on the outer layer of the layered structure when the tab is wrapped around the article. The layers of the Z-folded tab may be adherent to each other, for example by means of adhesive between the bottom and middle layer and between the middle and top layer, or as a result of the material of the layers being self-adherent, or as a result of one or more hook portions which releasably fasten to the tab itself.

In embodiments according to the disclosure, the at least one elongate tab may be stretchable. For example, the disposal tab may be stretchable to an extent that it is capable of being wrapped around the absorbent article.

In embodiments according to the disclosure, the at least one elongate tab may be a belt attached to the absorbent article provided for holding the article around the wearer's waist. The at least one elongate tab may also be a fastening tab attached to such a belt.

In a second aspect, which may be combined with the other aspects and embodiments described herein, the disclosure provides a method of manufacturing an absorbent article comprising a layered structure with an absorbent material sandwiched between at least two layers of the layered structure, the method comprising the steps of: (a) providing a layer of said layered structure and at least one elongate tab, wherein at least a first portion and a second portion of each tab are made of a predetermined material which is deformable by means of an energy source; (b) positioning each of said at least one elongate tab with respect to said layer, such that the first portion of the tab overlaps with the respective layer; (c) attaching the first portion of each of said at least one elongate tab to the said layer, thereby creating an attached portion; (d) forming hooks on the second portion of each of said at least one elongate tab, thereby creating a fastening portion provided for releasably engaging a landing zone on the absorbent article. Said steps of attaching the first portion and forming hooks on the second portion are performed simultaneously by deforming said predetermined material by means of said energy source.

According to the present disclosure, the weld of the attached portion and the hooks of the fastening portion are formed simultaneously by deformation by means of the same energy source. The first and second portions are therefore made of predetermined materials, preferably the same material, so as to be deformable by means of the same energy source, such as for example heat, ultrasonic vibrations, micro waves, infrared radiation or other. In this way, it is possible to form the hooks on the tab and weld the tab onto the layered structure simultaneously, i.e., in the same or substantially the same step in a production line. Furthermore, the need for adhesive to attach the tab to the layer may be avoided. In embodiments, a further area of hooks, i.e., a further fastening portion or several areas of hooks, i.e., several fastening portions may also be obtained in the same step, i.e., formed simultaneously as the weld of the attached portion and the hooks of the fastening portion by deformation by means of the same energy source.

In embodiments according to the disclosure, the at least one elongate tab may comprise a complete layer of said material or may be fully made of said material.

In embodiments according to the disclosure, said material may be a thermoplastic material and the energy source may be chosen from: heat, ultrasonic vibrations, micro waves, infrared radiation.

In embodiments according to the disclosure, further hooks may be formed on the first portion by deforming said predetermined material by means of said energy source, preferably simultaneously with forming the hooks on the second portion.

In embodiments according to the disclosure, the method may further comprise the step of folding said at least one elongate tab.

BRIEF DESCRIPTION OF THE DRAWINGS

The present disclosure will be discussed in more detail below, with reference to the attached drawings.

DESCRIPTION OF EMBODIMENTS

Figure 1:
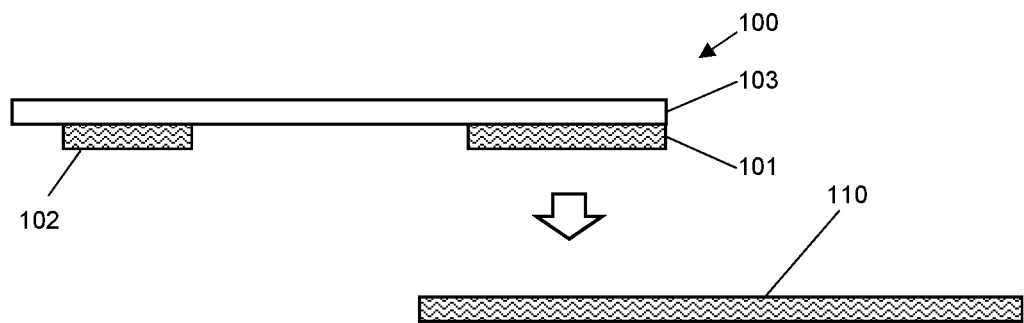
FIG. 1 shows a first exemplary embodiment of an elongate tab and a layer of a layered structure, before they are attached to each other.

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

As used herein, with "hooks" is intended to mean the hook parts or surface protrusions of a hook-and-loop type fastener which are adapted to be fastened to a zone comprising fibrous loops, referred to as the landing zone. The hooks can have any shape. Preferred examples of hooks comprise pins, for example straight pins, angled pins, curved pins, tapered pins, limbed or multi-limbed pins, hooks, limbed or multi-limbed hooks, mushroom shaped protrusions, palm tree shaped protrusions. The hooks may have any type of cross-section such as round, oval, square, rectangular, polygonal. The hooks preferably have a solid core. Within one fastening portion all hooks may have the same shape. Alternatively, one fastening portion may comprise several different shapes of hooks.

For the landing zone, any type of zone that is able to engage and preferably able to releasably engage with the surface protrusions can be considered. A landing zone can be a zone attached to the absorbent article, for example one or more landing zones attached to one or more side panels of the absorbent article, or a larger patch in the front portion of the absorbent article. Examples comprise a loop patch or a nonwoven, woven or knitted patch attached to the absorbent article for example by gluing, melting or stitching. Alternatively, the material of part of the absorbent article can act as landing zone, e.g., part or the whole outer cover of the absorbent article, or the material of one or more side panels. For example if the outer cover or part thereof, or the side panels, comprises a nonwoven.

The fastening portions described herein can include any number of hooks, possibly arranged in arrays or zones within the fastening portion. Further, the fastening portions can have various densities. By the "density" is meant herein the number of hooks per area unit (square inch or square mm). The density of the fastening portion may affect flexibility and softness of hook-and-loop type fasteners. For example, a lower density area generally provides higher material flexibility and softness. However, in order to provide a certain holding force between the engaging hooks and loops, a certain number of hooks should preferably be available for engagement.

"Absorbent articles" according to the present disclosure may refer to consumer products of the type which absorb and contain body exudates, and more specifically, refers to products which are placed against or in proximity to the body of the wearer to absorb and contain the various exudates discharged from the body. Absorbent articles, comprise, for example, diapers and incontinence devices. Diapers comprise for example all-in-one diapers, pant diapers and belt diapers. The diapers can be diapers for babies, young children or adults. Absorbent articles comprise a layered structure with an absorbent material sandwiched between at least two layers of said layered structure. For example, the absorbent material may be part of an absorbent core sandwiched between the layers structure, which for example may be a liquid-permeable topsheet and a liquid-impermeable backsheet. The absorbent article may comprise a front portion, a back portion and a crotch portion extending between the front portion and the back portion. Preferably, the front portion and/or the back portion comprises a waist portion. The waist portion is preferably stretchable or elastic So-called all-in-one diapers are characterized in that they include fastening tabs with which the front and rear portion of the diaper are joined when the diaper is applied around the waist of a user. The fastening tabs may be attached to the layered structure which comprises an absorbent material sandwiched between at least two layers of said layered structure.

So-called pant diapers are characterized in that the front and rear portion of the diaper are joined at the waist. This type of diaper is intended to be put on a user precisely like a pair of underpants, i.e., drawn over the user's legs. The joining at the waist part of the pant diapers can usually be broken open to remove the pant diapers from the user so that is not necessarily required to pull the pants down over the user's legs and feet to remove the pant diaper. Pant diapers normally comprise both elastic areas in the waist section and around the leg openings. Pant diapers that can be opened and reclosed by means of refastening means also exist. Such pant diapers can be opened for example to check the contents of the article or to adjust the width of the article and then reclosed afterwards.

So-called belt diapers are characterized in that they comprise a belt that is transverse oriented in relation to the absorbent part of the diaper and which is attached integrally with the chassis, i.e., attached to the layered structure which comprises the absorbent material sandwiched between at least two layers of said layered structure, or the absorbent part. The belt may have two belt portions extending on either side of the rear end or the front end of the chassis or the absorbent part. When putting on a belt diaper, the two belt portions are intended to be fastened around the waist of the wearer in a first stage. The front end or the rear end of the absorbent part of the belt diaper is hanging loose from the belt between the legs of the wearer. Once the belt portions have been joined together, the absorbent part is led between the user's legs and fastened to the belt, wherein the belt comprises fixing surfaces intended to stick to a fixing element arranged on the absorbent part of the diaper by its free transverse edge. Another type of belt diaper is in two pieces and comprises a separate belt and a separate absorbent structure. When in use the belt is fastened around the user's waist, following which the absorbent structure is joined to the outside of the belt by means of hook and loop elements or tape elements in the corners of the absorption structure.

The absorbent article according to the present disclosure can be a disposable article or a non-disposable article. The term "disposable" is used to describe absorbent articles which generally are not intended to be laundered or otherwise restored, or reused as an absorbent article, e.g., they are intended, to be discarded after a single use and may also be configured to be recycled, composted or otherwise disposed of in an environmentally compatible manner.

A disposal tab may be provided on the outside of a disposable article and intended for being wrapped around the article to enable the article to be disposed in a compact form with the absorbed fluids safely contained. The disposal tab generally has a part which is permanently attached to the article and a part which is releasable and possibly stretchable for being wrapped around the article.

In embodiments according to the present disclosure, the absorbent part of the absorbent articles is generally formed by a layered structure containing a core of absorbent material. The core may be sandwiched by a topsheet and a backsheet. The topsheet is permeable to the fluid(s) to be absorbed; the backsheet is impermeable to these fluids. Additional layers may be provided between the topsheet or backsheet and the core to improve absorption and/or retention of the fluids. A core wrap of for example nonwoven may enclose the core.

Embodiments of absorbent articles are described herein which comprise "side panels", also attached to the layered structure. The side panels of the absorbent article may comprise, for example, a polymer film or foil, a coated film or foil, for example a polymer coated film or foil, a textile substrate such as a woven structure or a nonwoven substrate or a coated textile substrate, for example a polymer coated textile structure. The side panel preferably comprises a thermoplastic material. Examples of thermoplastic materials comprise polyamide, polyolefin such as polypropylene and polyethylene, polystyrene such as styrene-isoprene-styrene (SIS), styrene-butadiene-styrene (SBS), styrene-ethylene-butylene-styrene (SEBS), acrylonitrile-butadiene-styrene (ABS), polyester, polycarbonate, polyvinyl chloride (PVC), polyetherester, polyetheramine, PLA, polylactic acid (polyester), thermoplastic starch, cellulose esters, polyhydroxyalkanoates (PHAs) like the poly-3-hydroxybutyrate (PHB), polyhydroxyvalerate (PHV), polyhydroxyhexanoate (PHH), and blends thereof. The thermoplastic material may be modified or reinforced for example with fillers, fibers, flame retardants, colorants, etc. It is clear for a person skilled in the art that the side panel may comprise multiple layers for example a laminate comprising two or three layers.

Embodiments of absorbent articles are described herein which comprise portions made of predetermined materials which are deformable by means of an energy source. The energy source is used to deform these portions, at least partly, to form a weld for attachment of layers as well as to form hooks of a hook-and-loop type fastener. Preferred materials are thermoplastic materials, deformable by means of an energy source such as for example heat, ultrasonic vibrations, micro waves, infrared radiation or other. In this way, it is possible to form of the hooks and the weld simultaneously, i.e., in the same or substantially the same step in a production line. Examples of preferred thermoplastic materials comprise polyamide, polyolefin such as polypropylene and polyethylene, polystyrene such as styrene-isoprene-styrene (SIS), styrene-butadiene-styrene (SBS), styrene-ethylene-butylene-styrene (SEBS), acrylonitrile-butadiene-styrene (ABS), polyester, polycarbonate, polyvinyl chloride (PVC), polyetherester, polyetheramine, PLA, polylactic acid (polyester), thermoplastic starch, cellulose esters, polyhydroxyalkanoates (PHAs) like the poly-3-hydroxybutyrate (PHB), polyhydroxyvalerate (PHV), polyhydroxyhexanoate (PHH), and blends thereof. The thermoplastic material may be modified or reinforced for example with fillers, fibers, flame retardants, colorants, etc.

A first embodiment of the disclosure is described with reference to FIGS. 1-3.

FIG. 1 schematically shows an elongate tab 100, which may be a fastening tab of a diaper. Fastening tabs (see FIG. 7) typically have a length L between 40 and 75 mm and a width W between 20 and 50 mm. The tab 100 comprises a carrier layer 103 which carries a first portion 101 and a second portion 102 of a predetermined material, preferably the same material, deformable by means of an energy source, in particular ultrasonic vibrations. The first portion 101 is used for attachment to a layer 110 of the layered structure of the absorbent article. The second portion 102 is used to form hooks and obtain a fastening portion 106 of a hook-and-loop type fastener.

The attachment and the forming of the hooks may be economically performed in a single process step by use of the same energy source and result in process steps in which the use of adhesive is avoided. As shown in FIG. 1 by the arrow, the tab 100 is appropriately positioned on the layer 110, following which the energy is applied to soften and deform the material of both portions 101, 102. An embodiment of such a deformation step is described further below.

Figure 2:
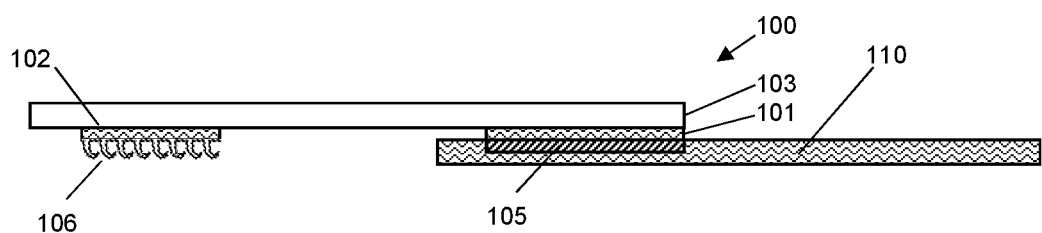
FIG. 2 shows a first exemplary embodiment of an elongate tab and a layer of a layered structure, after they are attached to each other.

The result after the deformation step is shown in FIG. 2. At portion 101, a weld 105 is formed from the deformed material (which can also include deformed material of the layer 110). At portion 102, the fastening portion 106 with hooks is formed.

The fastening portion 106 and the attached (welded) portion 105 are spaced from each other. They may be located, as shown, at or near opposite ends of the elongate tab 100. Preferably, the dimensions are such that the tab can be folded around the layer 110 with the fastening portion 106 located beyond the weld 105, so that the fastening portion 106 is releasably attachable to fibrous loops of the layer 110 in a region that has not been affected by the welding. FIG. 3 shows the result after this folding step.

The steps described with reference to FIGS. 1-3 may be performed on the layer 110 before, during or after the assembly of the layered structure. The layer 110 may be a layer of the layered structure or a layer which is in turn attached to the layered structure. The layer 110 may for example be a backsheet of a layered structure, a side panel which is attached to a layered structure, or a belt which is attached to a layered structure.

A second embodiment of the disclosure is described with reference to FIGS. 4-6.

Figure 4:
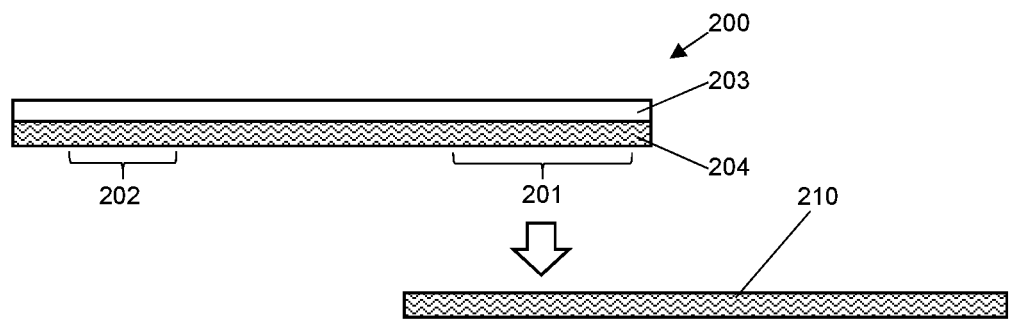
FIG. 4 shows a second exemplary embodiment of an elongate tab and a layer of a layered structure, before they are attached to each other.

FIG. 4 schematically shows an elongate tab 200, which may be a fastening tab of a diaper. The tab 200 comprises a laminate of a film 203 and a nonwoven layer 204 of a predetermined material, deformable by means of an energy source, for example ultrasonic vibrations. A first portion or zone 201 of the layer 204 is used for attachment to a layer 210 of the layered structure of the absorbent article by forming a weld 205. A second portion or zone 202 of the layer 204 is used to form hooks and obtain a fastening portion 206 of a hook-and-loop type fastener. In this embodiment, further hooks 207 are also formed at the first portion 201.

The formation of the weld 205 and the hooks 206, 207 may be economically performed in a single process step by use of the same energy source and result in process steps in which the use of adhesive is avoided. As shown in FIG. 4 by the arrow, the tab 200 is appropriately positioned on the layer 210, following which the energy is applied to soften and deform the material of both portions 201, 202. An embodiment of such a deformation step is described further below.

Figure 5:
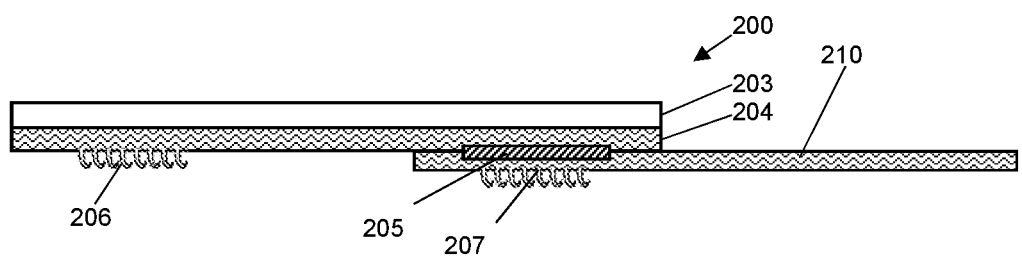
FIG. 5 shows a second exemplary embodiment of an elongate tab and a layer of a layered structure, after they are attached to each other.

The result after the deformation step is shown in FIG. 5. At portion 202, the fastening portion 206 with hooks is formed. At portion 201, a weld 205 is formed from the deformed material (which can also include deformed material of the layer 210) and hooks 207 are formed on this weld 205.

The fastening portion 206 and the attached (welded) portion 205 with the further hooks 207 are spaced from each other. They may be located, as shown, at or near opposite ends of the elongate tab 200. Preferably, the dimensions are such that the tab can be folded around the layer 210 with the fastening portion 206 located beyond the weld 205 and further hooks 207, so that the fastening portion 206 is releasably attachable to fibrous loops of the layer 210 in a region that has not been affected by the welding and forming of hooks 207.

Figure 6:
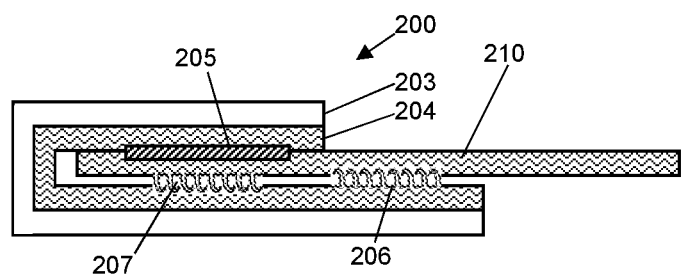
FIG. 6 shows a second exemplary embodiment of an elongate tab and a layer of a layered structure, after they are attached to each other and the tab is folded over.

FIG. 6 shows the result after this folding step. Both portions 206, 207 with hooks are protected by the folded tab and the hooks 207 function to ensure that the tab is held in this folded configuration during subsequent manufacturing steps and use until the user intentionally releases the tab 200 from the layer 210.

The steps described with reference to FIGS. 4-6 may be performed on the layer 210 before, during or after the assembly of the layered structure. The layer 210 may be a layer of the layered structure or a layer which is in turn attached to the layered structure. The layer 210 may for example be a backsheet of a layered structure, a side panel which is attached to a layered structure, or a belt which is attached to a layered structure.

Figure 7:
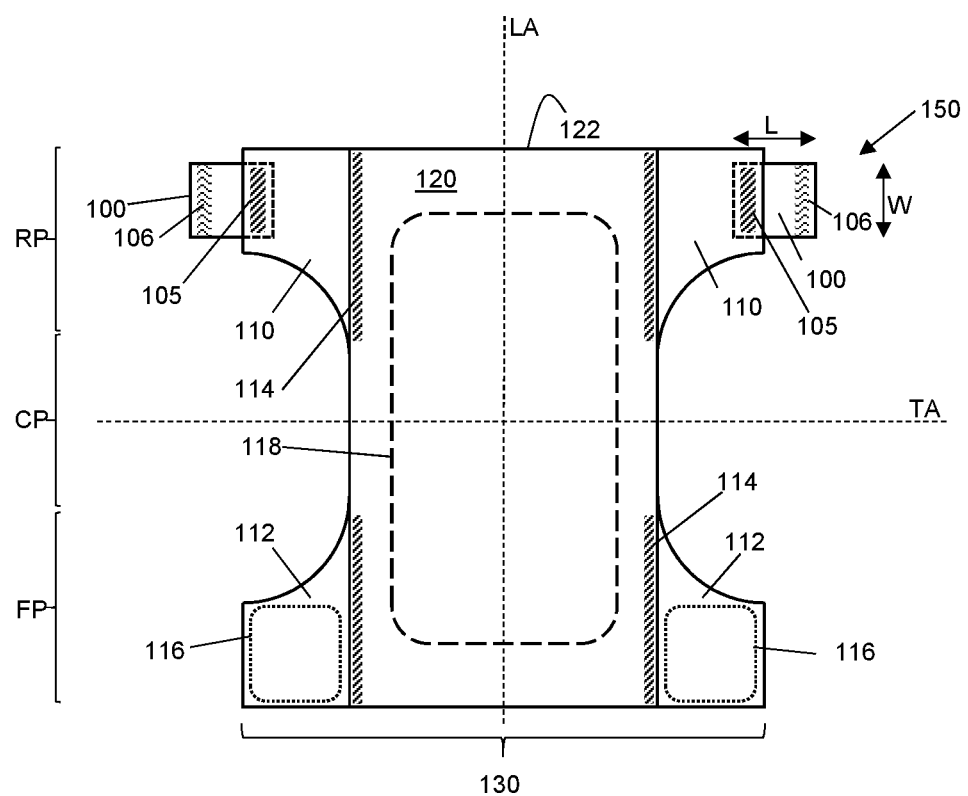
FIG. 7 shows a top view of an exemplary absorbent article according to the present disclosure.

FIG. 7 schematically shows a top view onto an embodiment of an absorbent article, such as a diaper with fastening tabs according to the disclosure. The diaper 150 is unfolded and in a flat state. The diaper comprises a layered structure 130 which is composed of a central part with a (permeable) topsheet 120 and a (impermeable) backsheet 122 on opposite sides of a core 118 of absorbent material. In other words, the diaper 150 comprises an absorbent core 118 sandwiched between a liquid-permeable topsheet 120 and a liquid-impermeable backsheet 122. The diaper being arranged along a longitudinal axis "LA" and a transversal axis "TA" extending in a perpendicular direction in relation to the longitudinal axis, said article comprising a front portion "FP", a back or rear portion "RP" and a crotch portion "CP" extending between the front portion and the back portion. The diaper has a longitudinal center line extending along the longitudinal axis. The front portion and the back portion each have a waist edge. The front portion is intended to be oriented in a direction towards the wearers belly during use of the article.

Preferably, the absorbent core 118 is disposed at least in the crotch portion "CP". The absorbent core is possibly extending in the front portion "FP" and in the rear portion "RP". The topsheet 120 is arranged at the surface of the diaper, i.e., at the side which is facing the wearer, whereas the backsheet 122 is arranged at the underside of the article. The absorbent structure, i.e., the core 118 is for absorbing body excudates from a wearer to provide a dry and comfortable fit for the wearer.

Various types of materials may be used for the absorbent article. The topsheet is arranged to face the wearer of the absorbent article when worn. The topsheet may be formed by a fluid permeable nonwoven fabric or film which is made of thermoplastic synthetic fibers. The topsheet may be sufficiently liquid-permeable to allow discharged body fluids to penetrate through the thickness of the topsheet. Also, the topsheet may be suitably manufactured from a material which is compliant and soft-feeling to the skin of the wearer. The topsheet may consist of a single layer or have a laminate structure comprising a plurality of layers, for example, two or more layers. The layers may be made of the same material, or some or all the layers may be made of different materials.

The layer of the topsheet or, for the case of a laminate structure, one, some, or all layers of the topsheet may be made of a single material or have plural portions made of different materials, e.g., within different parts of the wearer-facing surface of the topsheet.

The layer of the topsheet or, for the case of a laminate structure, one, some or all layers of the topsheet may be a nonwoven material, a perforated plastic film, a plastic or textile mesh, or a liquid permeable foam layer.

The layer of the topsheet or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 8-40 g/m2. However, the disclosure is not limited to topsheets having this basis weight only.

The backsheet may be constituted by a liquid-impermeable and breathable layer such as a polymeric film, for example a film of polyethylene or polypropylene. According to different embodiments, the materials which may be used for the backsheet 122 include thin and flexible fluid impermeable plastic films, or fluid impermeable nonwoven materials, fluid impermeable foams and fluid impermeable laminates.

The backsheet may be formed by a single layer, but may alternatively be formed by a multi-layered structure, i.e., a laminate, wherein at least one layer is fluid impermeable. Furthermore, the backsheet 122 may be elastic in any direction.

Furthermore, the backsheet may have a laminate structure comprising a liquid barrier sheet and a nonwoven layer arranged on top of each other (not shown in detail in the drawings), wherein the nonwoven layer is arranged at an outer side away from the wearer of the absorbent article when worn.

The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers.

The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like.

The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Furthermore, the absorbent core provided between the topsheet and the backsheet to absorb the liquid, such as urine or other bodily fluids, which has passed through the topsheet. The absorbent core may be made of one layer only, made from any suitable absorbent or liquid uptake material, such as one or more layers of cellulose fluff pulp, foam, fiber waddings or the like.

The absorbent core may comprise suitable amounts of superabsorbent particles. Such superabsorbent material is well known in the field of absorbent articles, and is constituted by a water-swellable and water-insoluble material which is capable of absorbing large quantities of fluid upon formation of a hydrogel. The absorbent core may contain superabsorbent material in the form of fibers or particles of absorbent polymer material. For example, the superabsorbent material may be surface cross-linked, partially neutralized polyacrylates. Furthermore, a core cover may surround the core and may be made of nonwoven material, with a basis weight of 5-20 g/m2.

The superabsorbent material, e.g., the superabsorbent fibers or particles, may be mixed with other absorbent or liquid uptake material or materials, such as cellulose fluff pulp, and/or arranged in pockets or layers in the absorbent core.

The absorbent core may further comprise components for improving the properties of the absorbent core. For example, the absorbent core may comprise a binder or binders, such as binder fibers.

Furthermore, as known by the skilled person, the various layers of the absorbent article may be attached by means of adhesive material.

One or more additional layers may be provided in the absorbent article. For example, an acquisition layer may be arranged between the absorbent core and the topsheet. Such an additional layer may for example be in the form of an airlaid layer, a spunlace layer, a high-loft, foam or any other type of material layer which may be used in an absorbent article to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum.

In the embodiment of FIG. 7, first and second side panels 110, 112 are attached to the longitudinal edges of the central part by means of welds 114 and in this way form part of the layered structure 130. The first side panels 110 are located at the rear body portion RP of the diaper and provided with fastening tabs 100 according to the embodiment of FIGS. 1-3, here attached to the back side of the panels 110 (i.e., the outside of the diaper 150), but the fastening tabs 100 could also be attached to the front side or a different layer. The second side panels 112 are located at the front body portion FP of the diaper. The back sides of the second side panels 112, i.e., the outer side, which is facing away from the user during use, provide landing zones 116 for the fastening portions 106 of the fastening tabs 100. In FIG. 7, the tabs 100 are shown in released position, i.e., released and unfolded by the user before use. In packaged condition, i.e., as the article is sold, the tabs 100 are normally in folded position as shown in FIG. 3. Instead of the separate side panels, both the topsheet and the backsheet may extend laterally outside the absorbent core along the perimeter of the absorbent article and form the side panels.

A third embodiment of the disclosure is described with reference to FIGS. 8-9, wherein the elongate tab 300 is a disposal tab, attached to an outer layer of the layered structure and provided for being wrapped around the absorbent article. A disposal tape is typically between 60 and 72 mm long in a Z-fold configuration. When unfolded the total length of the disposal tape may be about 100 to 200 mm. The width of a disposal tape is typically between 10 and 20 mm. Disposal tabs are typically attached to the backsheet of the diaper, for example in the middle of the rear body portion and oriented in longitudinal direction of the diaper, but it is evident that the disposal tab may be attached elsewhere on the article.

Figure 8:
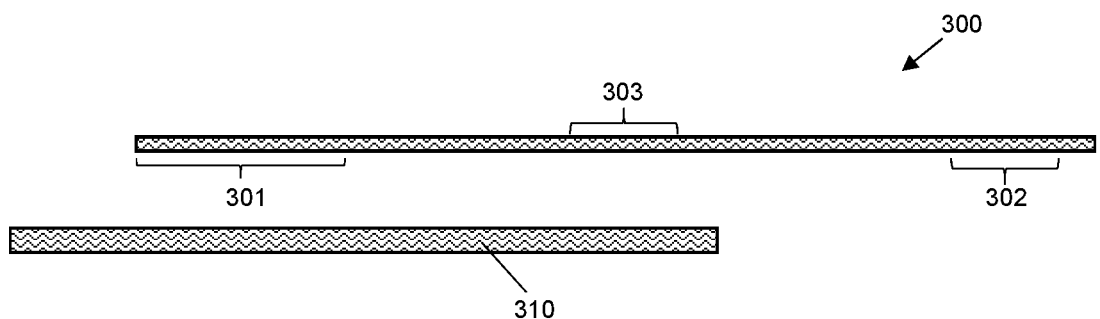
FIG. 8 shows a third exemplary embodiment of an elongate tab and a layer of a layered structure, before they are attached to each other.

FIG. 8 shows the tab 300 before it is attached to the layer 310, which may be the backsheet of the article. The tab is formed by a single layer of nonwoven. Three zones are defined on the tab: a first zone or portion 301 at one end for forming a weld 305 for permanent attachment to the layer 310, a second zone or portion 302 for forming hooks of a fastening portion 306 and a third zone 303 on the opposite side of the tab for forming further hooks 307. The weld 305 and the fastening portion 306 may be formed simultaneously in the same way as described for other embodiments described herein. The further hooks 307 may be formed in a preceding or subsequent step. If more material is needed to create the hooks 306, 307 and/or the weld 305, the single layer could be folded in these zones to create multiple layers of material.

Figure 9:
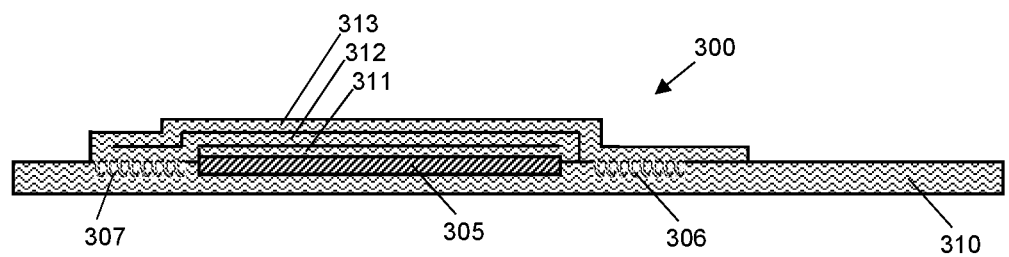
FIG. 9 shows a third exemplary embodiment of an elongate tab and a layer of a layered structure, after they are attached to each other and the tab is Z-folded onto itself.

FIG. 9 shows the tab 300 after attachment to the layer 310 and after being Z-folded. A bottom layer 311 of the Z-folded tab 300 comprises the attached portion which is attached to the outer layer 310 by means of the weld 305. A middle layer 312 lies on top of the bottom layer and comprises a portion with hooks 307 which extends beyond the bottom layer and is releasably fastened to the outer layer 310 of the absorbent article. A top layer lies 313 on top of the middle layer and comprises the fastening portion 306 which extends beyond the bottom and middle layers and is releasably fastened to the outer layer 310 of the absorbent article.

In use, when a user wants to dispose of the article, the user pulls the tab 300 at the end with the fastening portion 306 to release its hooks from the outer layer 310 and unfolds the tab, thereby also releasing the hooks 307 from the outer layer 310. The unfolded tab can subsequently be wrapped around the article and the fastening portion 306 subsequently fastened to a different region or landing zone on the article.

In alternative embodiments, the layers of a Z-folded disposal tab may be adherent to each other, for example by means of adhesive between the bottom and middle layer and between the middle and top layer, or as a result of the material of the layers being self-adherent.

In alternative embodiments, the elongate tab may be a belt attached to the absorbent article, for example to a backsheet, and provided for holding the article around the wearer's waist, i.e., the article then being for example a belt diaper. A belt diaper having a belt may have two belt portions i.e., two belts extending on either side of the rear end or the front end of the chassis or the absorbent part. When putting on a belt diaper the two belt portions, i.e., the two belts are intended to be fastened around the waist of the wearer in a first stage. The front end or the rear end of the absorbent part of the belt diaper is hanging loose from the belt between the legs of the wearer. Once the belt portions have been joined together, the absorbent part is led between the user's legs and fastened to the belt, wherein the belt comprises fixing surfaces intended to stick to a fixing element arranged on the absorbent part of the diaper by its free transverse edge For such an absorbent article, which comprises two belt portions only one of the belt portions may comprise a fastening portion to fasten the belts together when they overlap during use. Alternatively, both belts may have fastening portions in opposite directions, so that the fastening portion on the first belt attach the second belt and the fastening portion of the second belt attach the first belt when they are overlapping each other during use.

In a further alternative embodiment, the at least one elongate tab may also be one or more fastening tabs attached to such a belt. The embodiment of FIGS. 4-6 is for example suitable for obtaining such a construction, the layer 210 being the belt with a fastening tab 200 at one end, provided for being fastened to the second belt. In use, both portions with hooks 206 and 207 may be used for engaging the second belt.

In embodiments according to the disclosure, the at least one elongate tab, e.g., fastening tabs or disposal tabs as described above, may be stretchable, i.e., elastic. For example, the disposal tab may be stretchable to an extent that it is capable of being wrapped around the absorbent article, for example stretchable by 50 to 300%.

Figure 10:
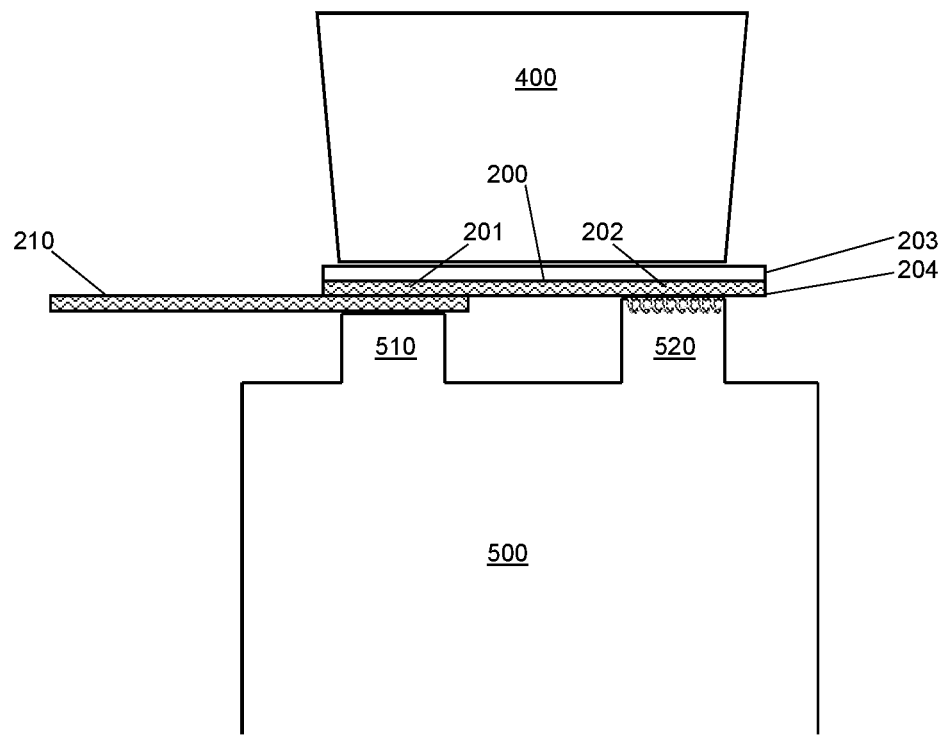
FIGS. 10 and 11 show exemplary embodiments of manufacturing steps according to the present disclosure.
Figure 11:
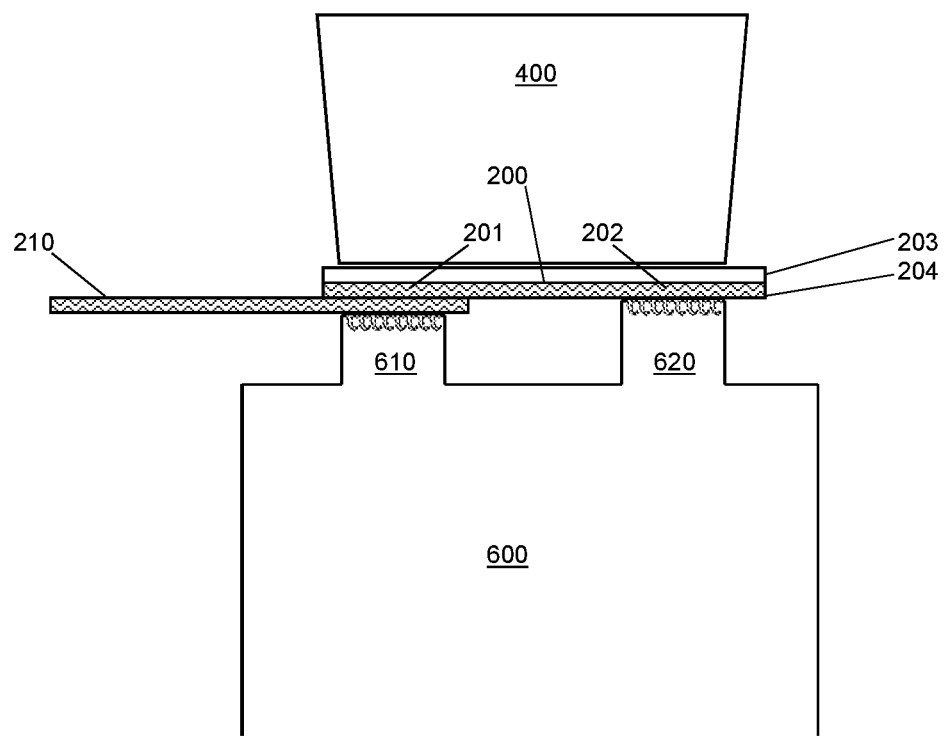

FIGS. 10 and 11 show embodiments of steps of the method of manufacturing the absorbent articles described herein, in particular, the steps of attaching the first portion 201 of an elongate tab 200 to the layer 210 of the layered structure and forming hooks on the second portion 202 of the elongate tab. These steps of attaching the first portion and forming hooks on the second portion may be performed simultaneously by deforming the predetermined material by means of the same energy source. In FIGS. 10 and 11, a tab according to FIGS. 4-6 is shown, but the steps can also be applied on the other elongate tabs described herein.

In the embodiments of FIGS. 10 and 11, ultrasonic vibrations are used as energy source. The process for forming surface protrusions using ultrasonic energy is known from WO 2010/085492 A1 and U.S. Pat. No. 6,746,434 B2. Here, this process is simultaneously used for forming a weld. To this end, the tab 200 and the layer 210 are positioned between an anvil 500, 600 and an ultrasonic horn 400. The anvil 500, 600 (shown in cross-section in FIGS. 10 and 11) may be a rotating anvil which has two annular protruding parts.

In the embodiment of FIG. 10, the first annular protrusion 510 has a flat top side. The second annular protrusion 520 has recesses in its top side, shaped for forming hooks. The first portion 201 and the layer 210 are positioned on top of the first annular protrusion and are welded together by application of the ultrasonic energy, i.e., the material of the first portion 201 of the layer 204 is here deformed to form the weld 205. The second portion 202 is positioned on top of the second annular protrusion 520 and is deformed by the ultrasonic energy into the fastening portion with hooks 206. The correct position may for example be verified by means of a vision system.

In the embodiment of FIG. 11, the anvil 600 likewise has two annular protrusions 610, 620. In this embodiment, the first annular protrusion 610 also has recesses in its top side, shaped for forming hooks. Here, the first portion 201 and the layer 210 are not only welded together, but simultaneously hooks 207 are also formed in the region of the weld 205 (see FIG. 5).

As an alternative, the ultrasonic horn 400 could have recesses, as for example to form hooks in the other direction (i.e., on the top side of the tab in the orientation shown in FIGS. 10 and 11) or in two different directions (i.e., on both sides of the tab).

Figure 3:
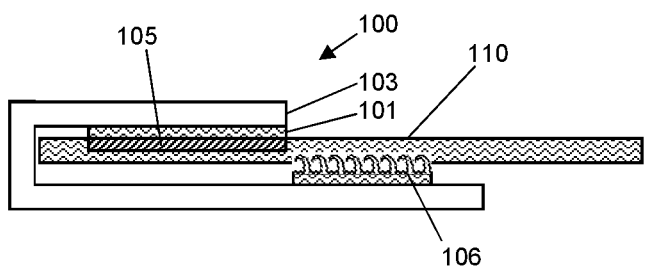
FIG. 3 shows a first exemplary embodiment of an elongate tab and a layer of a layered structure, after they are attached to each other and the tab is folded over.
Figure 12:
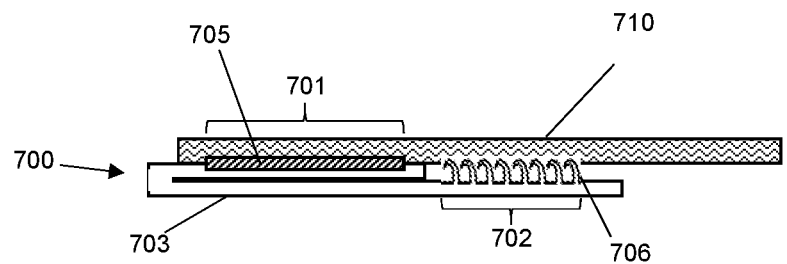
FIG. 12 shows a fourth exemplary embodiment of an elongate tab and a layer of a layered structure, after they are attached to each other and the tab is folded over.

FIG. 12 shows an alternative embodiment to that of FIGS. 1-3 wherein the tab 700 is made of a single layer 703 of the predetermined material. The fastening portion 706 and the weld 705 are formed by deformation of zones 702 and 701 of this layer 703. If more material is needed to create the surface protrusions in zone 702 and/or the weld in zone 701, the single layer 703 could be folded in the zones 701, 702 to create multiple layers of material. In this embodiment, the tab 700 is welded to the same surface of the layer 710 of the layered structure onto which the tab is folded and releasably fastened by means of the fastening portion 706.

Figure 13A:
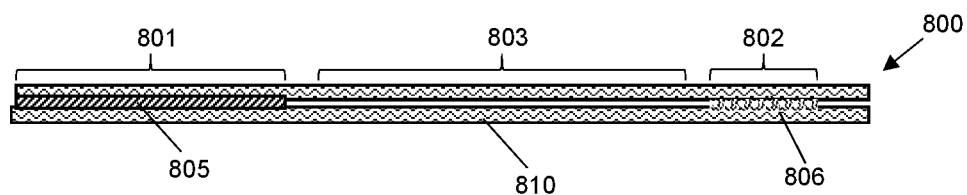
FIGS. 13A-B show a fifth exemplary embodiment of an elongate tab and a layer of a layered structure, attached to each other, the tab being stretchable.
Figure 13B:
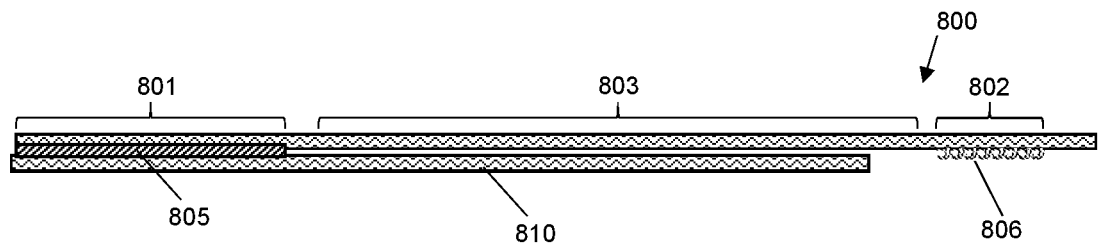

FIGS. 13A-B show an alternative embodiment to that of FIGS. 7-8 wherein the tab 800 is stretchable, for example a stretchable disposal tab. The tab comprises a layer of the predetermined, deformable material. The fastening portion 806 and the weld 805 are formed by deformation of zones 802 and 801 of this layer. A stretch zone 803 is provided between the fastening portion 806 and the attached portion 805. FIG. 13A shows the tab with the fastening portion 806 releasably fastened to the layer 810 of the layered structure; FIG. 13B shows the tab with the fastening portion 806 released and the tab stretched, for example for wrapping it around the article.

The invention claimed is:

1. An absorbent article comprising a layered structure with an absorbent material sandwiched between at least two layers of said layered structure and at least one elongate tab, each elongate tab comprising an attached portion by which the at least one elongate tab is permanently attached to at least one layer of the layered structure and spaced from the attached portion, a fastening portion with hooks provided for releasably engaging a landing zone on the absorbent article, wherein:

the at least one elongate tab comprises a complete layer of a predetermined thermoplastic material which is deformable of an energy source chosen from: heat, ultrasonic vibrations, micro waves, and infrared radiation;

at least the attached portion and the fastening portion of each of the at least one elongate tab are made from said layer of predetermined thermoplastic material, wherein the attached portion comprises a weld, the weld of the attached portion and the hooks of the fastening portion being integrally formed deformations of said predetermined thermoplastic material; and further hooks are formed on the elongate tab and/or the layered structure, the further hooks and the weld being on top of each other, the further hooks being integrally formed deformations of the predetermined thermoplastic material of the attached portion and/or of a material of the at least one layer of the layered structure.

2. The absorbent article according to claim 1, wherein the at least one elongate tab is fully made of said predetermined thermoplastic material.

3. The absorbent article according to claim 1, wherein said predetermined thermoplastic material is a thermoplastic material deformable by ultrasonic vibrations.

4. The absorbent article according to claim 1, wherein the at least one elongate tab includes fastening tabs attached to first side portions of the layered structure and configured for being fastened to one or more landing zones on a surface of the layered structure.

5. The absorbent article according to claim 4, wherein the first side portions are first side panels of the layered structure.

6. The absorbent article according to claim 4, wherein said landing zones are provided by second side panels of the layered structure.

7. The absorbent article according to claim 5, wherein the first side panels and/or the second side panels comprise at least one layer of a nonwoven material.

8. The absorbent article according to claim 7, wherein said nonwoven material is a thermoplastic material deformable by an energy source chosen from: heat, ultrasonic vibrations, micro waves, infrared radiation.

9. The absorbent article according to claim 4, wherein the fastening tabs are each welded to a first surface of a respective one of the first side portions and folded such that the fastening portion releasably engages said first surface of the respective one of the first side portions, or a second surface of the respective one of the first side portions opposite the first surface.

10. The absorbent article according to claim 1, wherein the further hooks are provided in the region of the weld so as to releasably engage a further portion of the folded fastening tab.

11. The absorbent article according to claim 1, wherein the at least one elongate tab is a disposal tab attached to an outer layer of the layered structure and configured for being wrapped around the article.

12. The absorbent article according to claim 11, wherein the disposal tab is a Z-folded tab, a bottom layer of the Z-folded tab comprising the attached portion and a top layer of the Z-folded tab comprising the fastening portion.

13. A method of manufacturing an absorbent article comprising a layered structure with an absorbent material sandwiched between at least two layers of the layered structure, the method comprising the steps of:

a) providing said layered structure and at least one elongate tab, wherein each of the at least one elongate tab comprises a complete layer of a predetermined thermoplastic material which is deformable by an energy source chosen from: heat, ultrasonic vibrations, micro waves and infrared radiation;

b) positioning each of said at least one elongate tab with respect to said layered structure, such that a first portion of said complete layer of the tab overlaps with a respective layer of the layered structure;

c) attaching the first portion of each of said at least one elongate tab to the respective layer, thereby creating an attached portion; and d) forming hooks on a second portion of each of said at least one elongate tab which is spaced from the first portion, thereby creating a fastening portion provided for releasably engaging a landing zone on the absorbent article, wherein said steps of attaching the first portion and forming hooks on the second portion are performed simultaneously by deforming said predetermined thermoplastic material by said energy source.

14. The method according to claim 13, wherein the at least one elongate tab is fully made of said predetermined thermoplastic material.

15. The method according to claim 13, wherein said predetermined thermoplastic material is a thermoplastic material deformable by ultrasonic vibrations.

16. The method according to claim 13, further comprising forming further hooks on the first portion by deforming said predetermined thermoplastic material by said energy source.

17. The method according to claim 16, wherein the deforming of said predetermined thermoplastic material by said energy source is performed simultaneously with the forming of the hooks on the second portion.

18. The method according to claim 13, further comprising the step of folding said at least one elongate tab.

* * * * *